Figure 1:
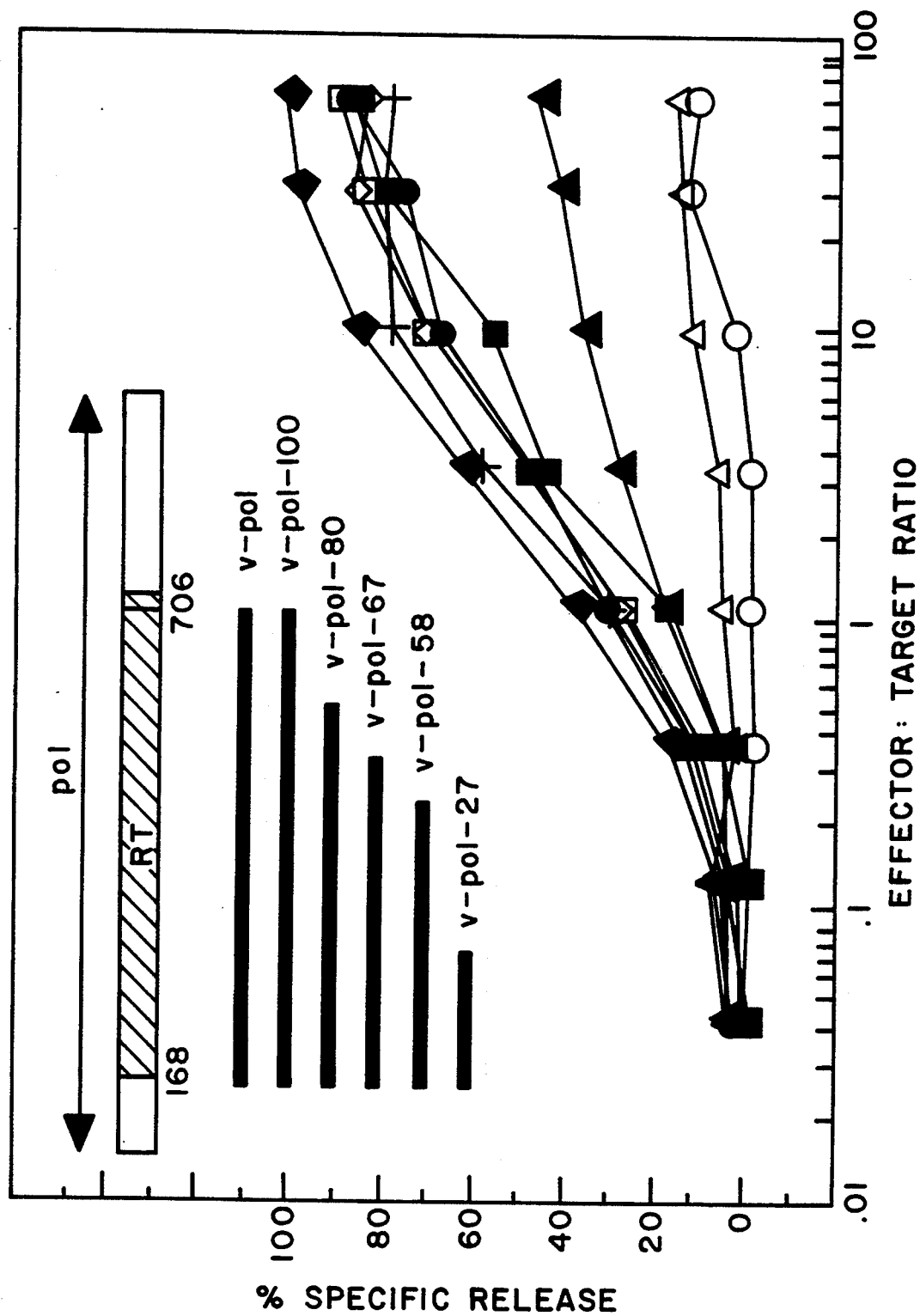

United States Patent [19]

Berzofsky et al.

[11] Patent Number: 5,336,758
[45] Date of Patent: Aug. 9, 1994

[54] PEPTIDES STIMULATING CYTOTOXIC T CELLS IMMUNE TO HIV RT

[75] Inventors: Jay A. Berzofsky; Anne Hosmalin; Mario S. Clerici, all of Bethesda; Ronald N. Germain, Potomac; Gene Shearer, Bethesda; Bernard Moss, Bethesda; Charles D. Pendleton, Bethesda, all of Md.

[73] Assignee: The United States of America as represented by the Department of Health and Human Services, Washington, D.C.

[21] Appl. No.: 489,825

[22] Filed: Mar. 9, 1990

[51] Int. Cl.[5] .................... A61K 37/02; C07K 7/08
[52] U.S. Cl. .................................... 530/326; 435/5; 435/69.3; 424/188.1
[58] Field of Search .................... 530/326; 514/14, 13; 435/5, 69.3; 424/88

[56] References Cited

U.S. PATENT DOCUMENTS 4,643,988  2/1987  Segrest et al. ................ 514/12

OTHER PUBLICATIONS

Alizon et al., Cell. vol. 46, 63–74, Jul. 4, 1986.
Ex parte Balzanini, 21 USPQ2d 1982, 1991.
Delisi, C. et al., Proc. Natl. Acad. Sci., 82:7048–7052, Oct. 1985.
Hosmalin, A. et al., Proc. Natl. Acad. Sci., 87:2344–2348, Mar. 1990.
Walher, B., Proc. Natl. Acad. Sci., 86:9514–9518, Dec. 1989.
Walher, B. et al., Science, 240 (4848):64–66, Apr. 1, 1988.
Hosmalin, A. et al., FASEB, J4 (7). pp. A2262, Jun. 1990.
Stedman's Medical Dictionary (24th Ed.), Williams & Wilkins, p. 26.

Primary Examiner—Lester L. Lee
Attorney, Agent, or Firm—Cushman, Darby & Cushman

[57] ABSTRACT

The subject invention relates to a peptide having the amino acid sequence Glu-Ile-Cys-Thr-Glu-Met-Glu-Lys-Glu-Gly-Lys-Ile-Ser-Lys-Ile-Gly-Pro or portions thereof. This peptide is derived from, or based upon, a region of a relatively conserved epitope of HIV-1 reverse transcriptase. The peptide may be utilized in the treatment of patients having human immunodeficiency virus or in the prevention of infection of those individuals who have been exposed to the disease, yet have not become sero-positive. The preparation containing the peptide may be administered either subcutaneously, intramuscularly or intravenously.

3 Claims, 5 Drawing Sheets

PEPTIDES STIMULATING CYTOTOXIC T CELLS IMMUNE TO HIV RT

T-cell mediated cytotoxicity plays an important role in control of infection by human immunodeficiency virus (HIV). A relatively conserved epitope of HIV-1 reverse transcriptase (RT) recognized by both murine and human cytotoxic T cells has been identified and characterized. The peptides of the invention elicit cytotoxic T cells which kill cells which produce reverse transcriptase of HIV. Since the reverse transcriptase of HIV is conserved to a greater degree than many other HIV proteins, this approach provides a vaccine component that is less affected by mutation of the HIV virus. Hence, the peptides of the invention provide a means of producing an immunologic response against a broad range of strains of the HIV virus.

Abbreviations

ADCC, antibody-dependent cellular cytotoxicity; CTL, cytotoxic T lymphocyte (s); EBV, Epstein-Barr virus; HIV, human immunodeficiency virus; L-pol, DAP3 fibroblast cell clone transfected with the HIV-1 RT gene; MHC, major histocompatibility complex; NK, natural killer cells; PBMC, peripheral blood mononuclear cells; RT, reverse transcriptase; v-pol, recombinant vaccinia virus containing the HIV-1 RT gene; v-ctrl, negative control recombinant vaccinia virus.

BACKGROUND OF THE INVENTION

Cytotoxic T lymphocytes (CTL) have been found to mediate protection in vivo against certain virus-induced diseases, including some caused by retroviruses (1-3). This defense mechanism might be particularly relevant against HIV, which can spread through cell-cell contact, and thus may not be accessible to antibody neutralization. Indeed, CD8+ cells have been shown to inhibit growth of HIV or SIV in cells of infected patients or monkeys (4,5). Efforts have thus been directed at studying the CTL response against different proteins of HIV. Human CD3+8+ CTL specific for the envelope glycoprotein gp160 have been identified (6-12), and an immunodominant CTL epitope has been mapped in H-2$^d$mice to residues 315-329, a highly variable region of the envelope (13). However, immunizing with the whole envelope protein is not an ideal approach for several reasons. First, the majority of the cytotoxic response assayed in vitro with fresh PBMC from HIV seropositive individuals seems to be mediated by non-MHC restricted mechanisms (ADCC or NK) (14). Second, the envelope is highly variable in sequence and CTL clones can distinguish different isolates of HIV (15,16). Third, there is evidence for antibody-dependent enhancement of HIV-1 infection, likely to be mediated by anti-envelope antibodies (17,18). Fourth, immune responses to the HIV envelope have been suggested to contribute to immune deficiency: Uninfected CD4+ T cells which bind gp120 may be killed by ADCC triggered by anti-envelope antibodies (19) or by CD4+ CTL specific for gp120 (20). Anti-gp120 antibodies can also inhibit CD4+ T-cell function like anti-CD4 antibodies by binding to gp120 which binds to CD4 (21). Also, gp160 can elicit autoantibodies that crossreact with human Class II MHC molecules and inhibit T-cell function (22). Finally, gp120 itself may inhibit T-cell function directly (19).

In contrast to the envelope glycoprotein, the internal proteins of HIV are more conserved and would be less likely to contribute to these deleterious effects. Moreover, in other vital models, internal proteins are the predominant targets of the CTL response (23-28). Responses have been found in HIV patients against the products of the gag, pol, nef and vif genes (7,9,12,-29,30). Because of its conservation and importance to vital function, the reverse transcriptase (RT) appears worthy of particular interest in this regard. We describe here our approach of using a murine model to identify evolutionarily conserved CTL determinants in RT and the relevance of this identification to human anti-HIV cytotoxic responses.

LEGENDS TO FIGURES

FIG 1. CTL Line Pol a specificity for the N-terminal end of HIV-1 reverse transcriptase. (A) pol gene arid the fragment inserted in the recombinant vaccinia virus v-pol and transfected into the fibroblast clone L-pol. The amino acid sequence is deduced from the nucleotide sequence (32). The recombinant viruses v-pol-100 to -27 contained 3'truncated gene fragments as described in the Methods and in ref. (33). (B) Pol a line specific cytotoxicity on L-pol, L-cells infected with v-pol or with truncated pol gene-recombinant vaccinia viruses. ○, L cells; ●, L cells+v-pol; □, L cells+v-pol-100; ■, L cells+v-pol-80; ◊, L cells+v-pol-67; ◆, L cells+v-pol-58; +, L cells+v-pol-27; △, L cells+v-crtl; ▲, L-pol.

Figure 2:
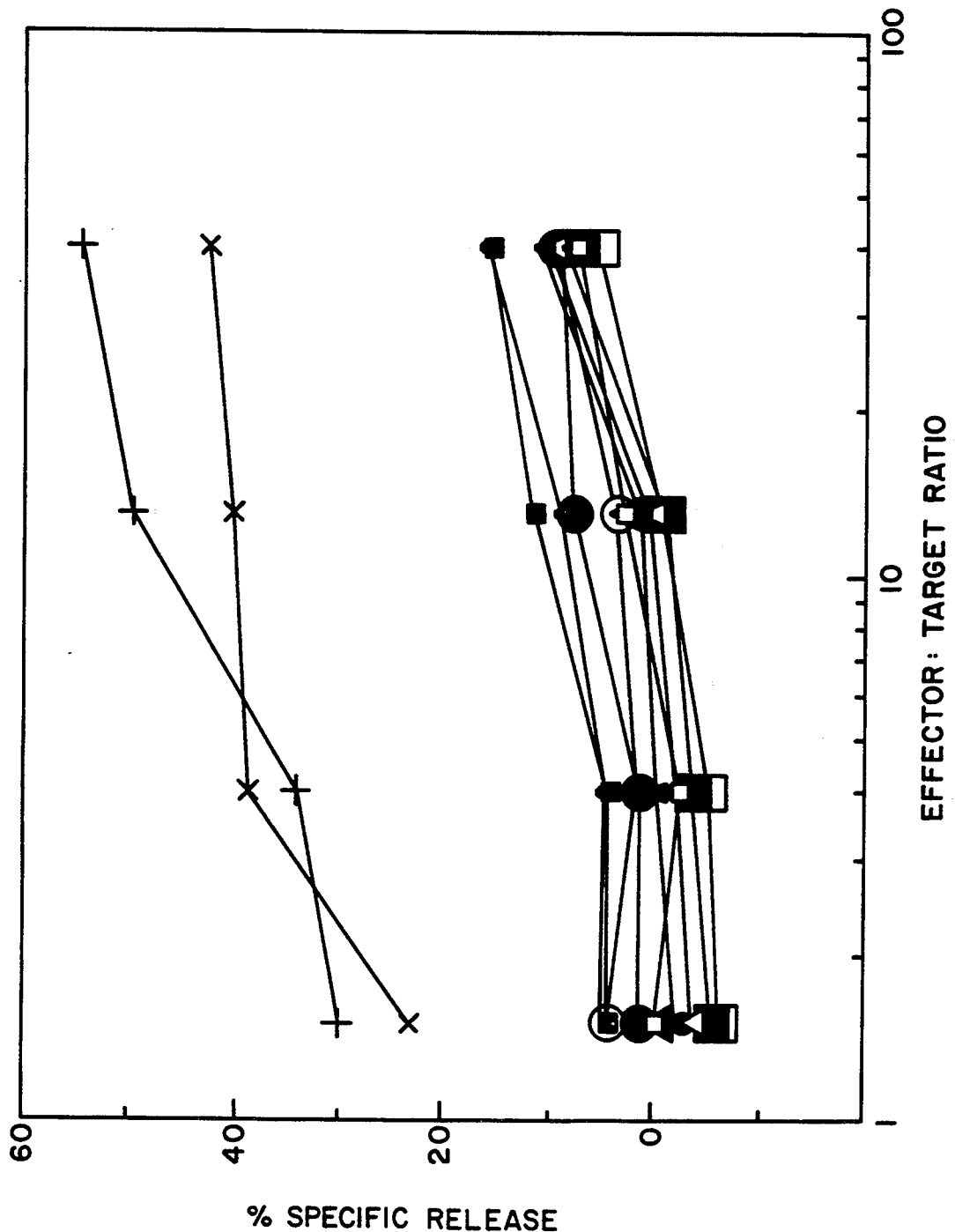

FIG. 2. CTL line Pol a specificity for peptide HP138. L-cells were incubated overnight with peptides at a concentration of 20 μm and with $^{51}$Cr as described in the Methods, then used as targets with different numbers of Pol a effector cells. The sequences of the peptides are following: HP 134: (175-189), HP 135: (185-199), HP 136: (193-207), HP 137: (199-213), HP 138: (205-219), HP 139: (215-229), HP 140: (299-244), HP 141: (238-252), HP 142: (243-2.57), HP 144: (265-279), HP 145: (275-289), HP 146: (283-297), HP 147: (288-302), HP 148: (300-314), HP 149: (311-325), HP 150: (315-329), HP 151: (324-339), HP 152: (329-343), HP 154: (355 -369). HP 143 (255-269) and HP 153 (344-359) could not be tested because they were insoluble. +, L-pol; ○, L cells; ●, L cells+HP 134 +HP 146; □, L cells+HP 135+HP 147; ■,L cells+HP 136; △, L Cells+HP 137+HP 148; ×, L cells+HP 138; ▲, L cells+HP 139+HP 149; □L cells+HP 140+HP 150; ■, L cells+HP 141+HP 151; △, L cells+HP 142+HP 152; ▲, L cells+HP 144+HP 154; ◆, L cells+HP 145+HP 155.

Figure 3:
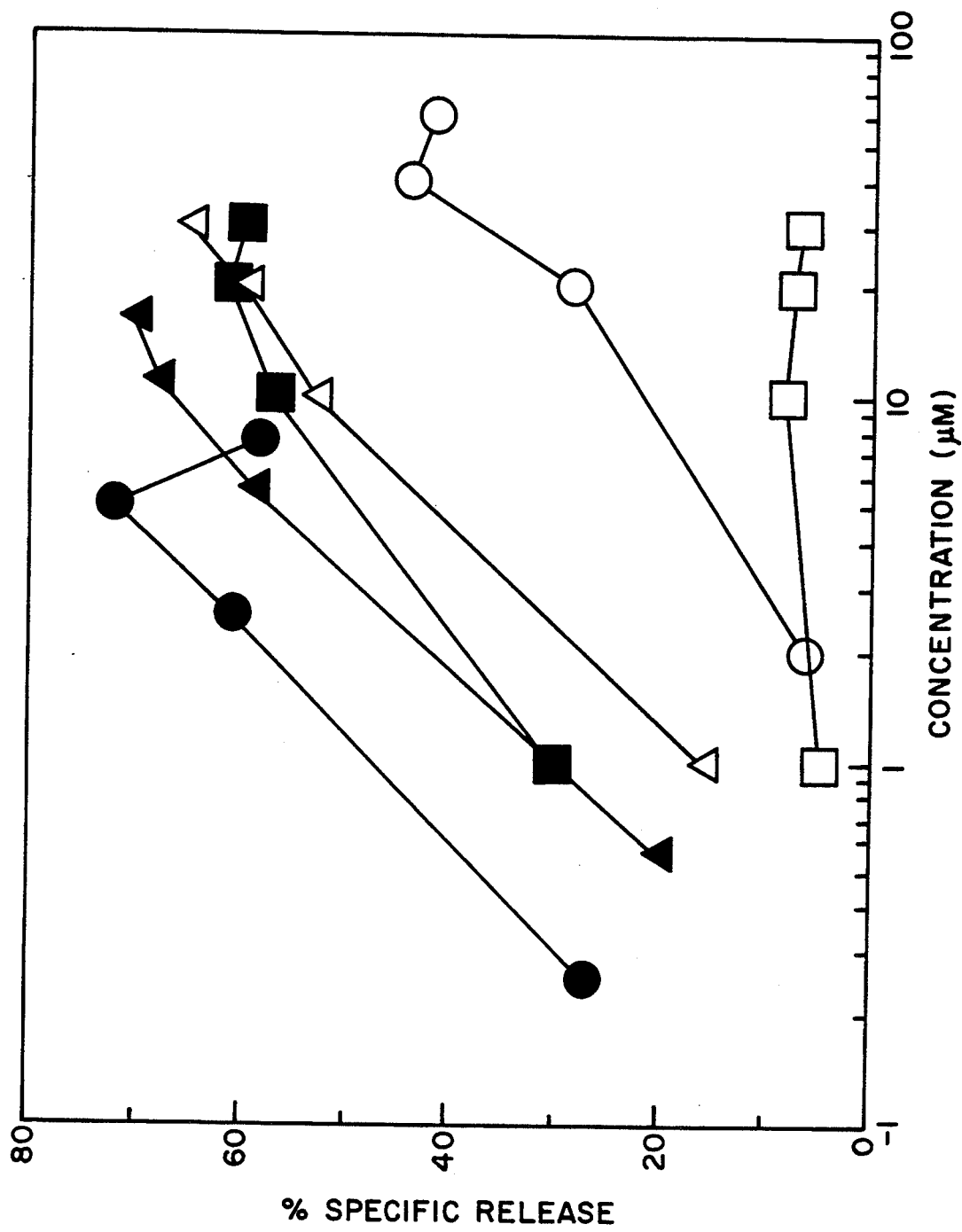

FIG. 3. Localization of the CTL epitope in the pol 199-223 area, ○, 205-219; ●, 203-219; □, 207-223; ■, 205-223; △, 199-223; ▲, 203-218. 205-219, which is the sequence of HP138, has been resynthesized along with its analogs.

Figure 4:
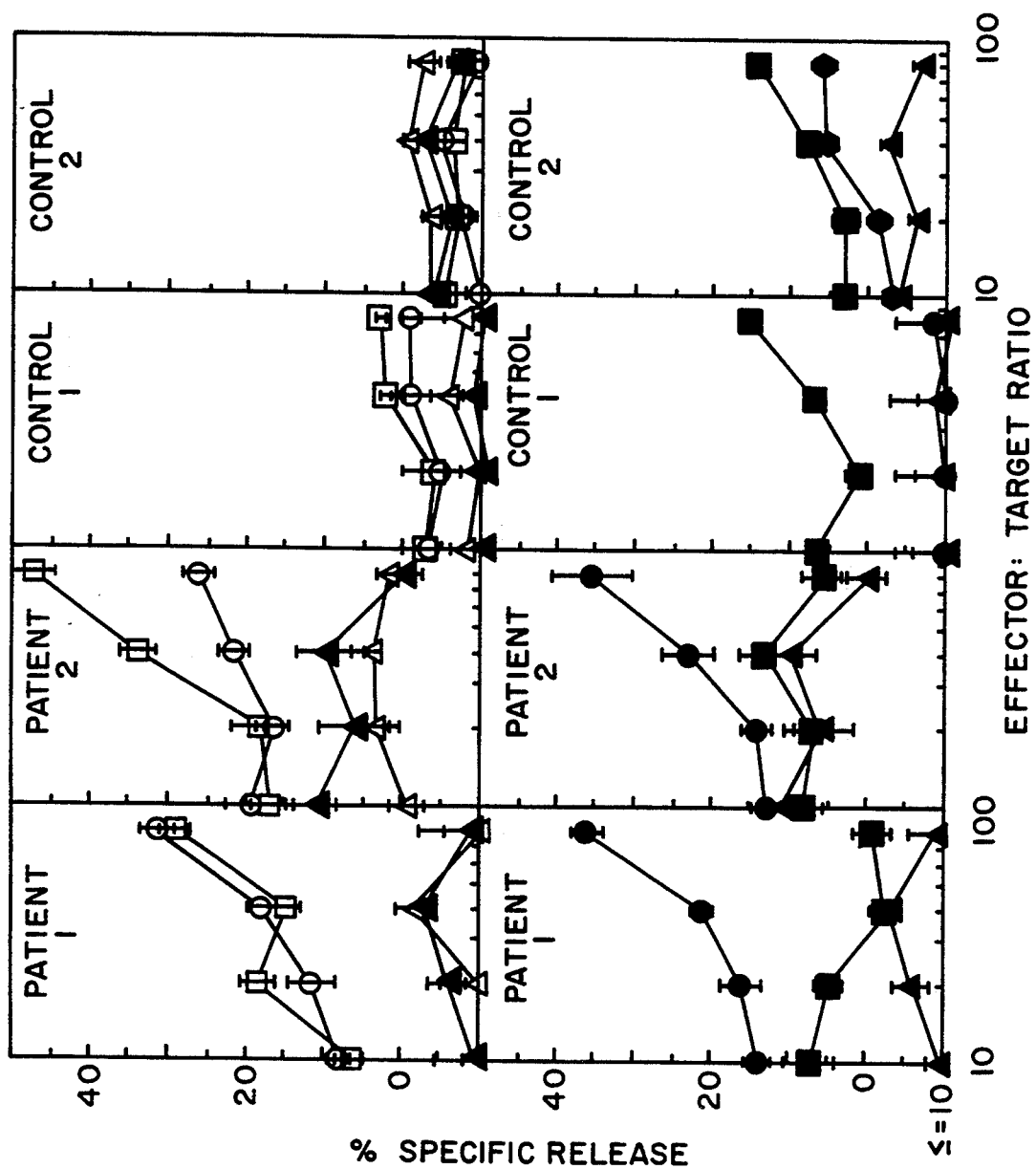

FIG. 4. Recognition of the immunodominant murine epitope of HIV-1 RT by peripheral blood cells from two HIV infected patients and two seronegative controls. EBV-transformed B cells derived from HIV infected donors or HIV$^-$ controls were used as targets as described in the Methods. Aliquots of each individual's target cells were incubated overnight with a concentration of 10 μm of peptides 203-219 (□), 205-219(○) or 255-269 (△) (HP 145, a control peptide without any activity in the murine tests as shown in FIG. 2, and not predicted to be a T-cell epitope by the AMPHI algorithm (43)). Other aliquots of target cells were infected with v-pol (●) or with v-ctrl (■). The targets were then assayed with autologous PBMC as effectors in a 6hr $^{51}$Cr release assay. The error bars show the standard error of the mean of the triplicates (SEM). Upper panel, targets pre-incubated with peptides. Lower panel, targets infected with viruses. ▲, targets pre-incubated in medium only.

Figure 5:
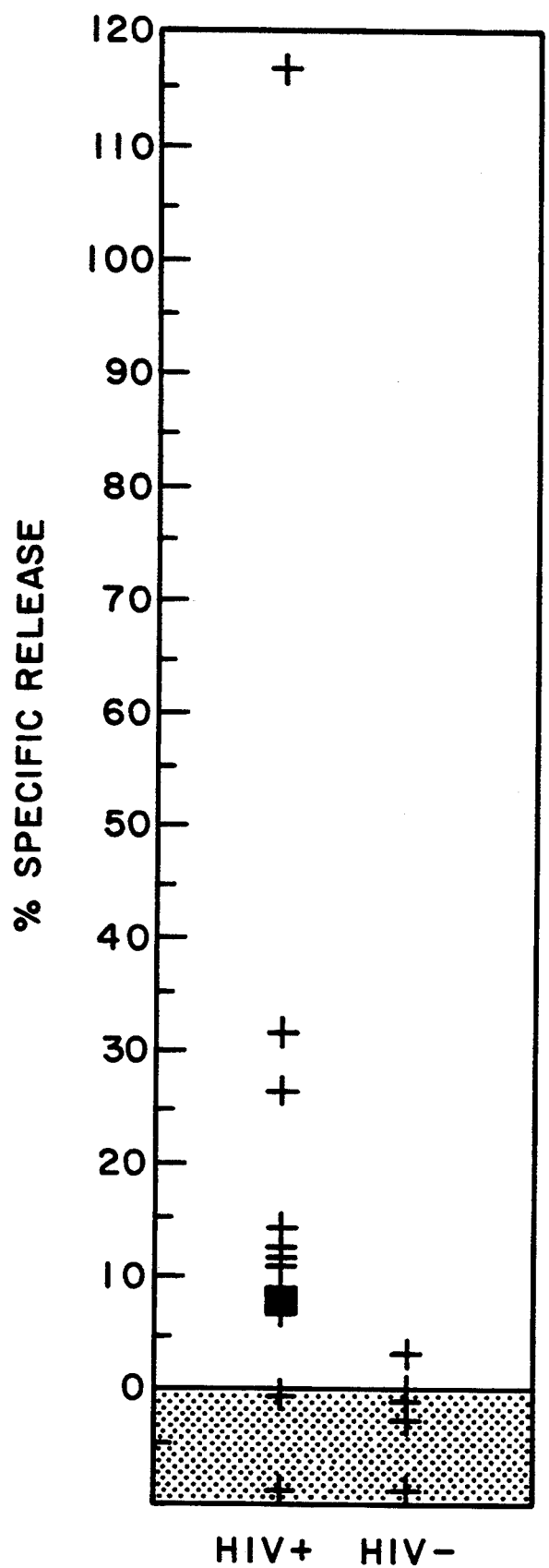

FIG. 5, Lysis of target cells incubated with 205-219 by autologous PBMC. Comparison of all the seropositive patients (HIV+) and the seronegative controls (HIV−). Each point represents the % specific $^{51}$Cr release of peptide-incubated targets after a 6 hr assay in presence of autologous PBMC at the maximal E:T ratio tested (80 or 40: 1). For each HIV+ donor, control target cells either with no peptide or with control vaccinia virus were not lysed. Two patients who had % specific releases at 11 and 12%, respectively, were not included in this figure because no adequate negative control was available.

SUMMARY OF THE INVENTION

T-cell mediated cytotoxicity plays an important role in control of infection by the human immunodeficiency virus (HIV). A relatively conserved epitope in the HIV-1 reverse transcriptase recognized by both murine and human cytotoxic T cells has been discovered. This epitope was identified using a murine antigen-specific CD8+ Class I MHC-molecule-restricted cytotoxic T-cell (CTL) line, a transfected fibroblast cell line expressing the HIV-1 pol gene, recombinant vaccinia viruses containing different truncated versions of the pol gene, and overlapping synthetic peptides. The optimal antigenic site was identified as residues 203-219 by synthesizing extended or truncated peptide analogs of the antigenic fragment. The optimal peptide was then tested for sensitization of autologous EBV-transformed B cell targets for killing by fresh human peripheral blood mononuclear cells. The peptide was recognized by CTL from several HIV seropositive patients but not from any seronegative donor. Hence, this peptide is a good immunogen for inclusion in an AIDS vaccine. The data demonstrates that the same CTL epitope can be seen by murine and human CD8+ CTL, as previously demonstrated for epitopes recognized by CD4+ helper T cells, and indicates the utility of screening for immunodominant CTL epitopes in mice prior to carrying out studies in humans.

Although consistent with an amphipathic $3_{10}$ helix, these peptides are not strongly predicted by any of the known predictive methods. Hence, the peptides would not have been selected by one of ordinary skill in the art as a likely candidate T cell epitope peptides.

MATERIALS AND METHODS

Mice. C3H/HeJ (H-2k) mice were obtained from the Jackson Laboratories (Bar Harbor, Me., USA).

Recombinant vaccinia viruses

V-pol (vCF-21, FIG. 1) (31) and v-pol-100 are recombinant vaccinia viruses containing the RT gene of HTLVIII subclone HXB.2 except for the last 22 residues (pol gene deduced amino acid sequence 168-706 for the insert, 168-728 for RT) (32). The truncated pol gene-recombinant vaccinia viruses (vCF 32, 33, 34, 35, and 37) (33) have been re-named in this application v-pol-100, -80, -67, -58, and -27, respectively, to indicate the proportional length of their inserts as a % of the v-pol-100 insert length (FIG. 1). These inserts all initiate at the 5' end of the original insert, corresponding to residue 168 of the amino acid sequence and to the N-terminal end of the processed protein. v-ctrl (vSC-8) (34) contains the E. coli lac-Z gene as a control.

Transfectants

The transfectant L-pol was prepared using the pcEXV-3 vector containing the same RT-encoding insert as v-pol. pcEXV-3-pol was cotransfected with pSV2neo into DAP-3 L cells using the CaPO4 method (35) and clones were isolated after selection in G418. A single clone (RGT 1.10.7) having a high level of pol transcripts in RNA dot-blot analysis was selected for use in these experiments. The control L cells (L28) were prepared with pSV2 neo alone.

Generation of a murine CTL line

The line Pol a was obtained from v-pol immunized (107 PFU IV) C3H/HeJ female mouse spleen cells restimulated in vitro with mitomycin-C treated L-pol transfectants as in (13) ($5 \times 10^6$ spleen cells, $5 \times 10^5$ L-pol cells/well in 24-well plates), but in presence of supplemented medium, i.e. complete T-cell medium containing 10% Concanavalin A stimulated rat spleen cell medium (T-cell Monoclone, Collaborative Research Inc., Bedford, Mass.). The line has been maintained now for more than a year by weekly restimulations ($0.3 \times 10^6$ line cells, $10^6$ L-pol cells) and bi-weekly feeding with supplemented medium. It has been used for assays not earlier than 3 days after a T-cell Monoclone addition.

CTL assay

The murine CTL assays were performed as in reference (13), with the following differences: $10^6$ L-cells were infected with recombinant vaccinia viruses at a multiplicity of infection of 50 for 1 hour, then washed and incubated overnight with $^{51}$Cr; in other experiments, L-cells were incubated overnight with peptides and with $^{51}$Cr ($0.3 \times 10^6$ cells, 0.05 mCi (1.85 MBq)/well in 24-well plates). The target cells were then washed four times before use in the 6-hour assay (5000 target cells/well in 96 round-bottom well plates). In the human assays, lines derived from peripheral blood mononuclear cells (PBMC) of donors by Epstein-Bart virus (EBV) transformation were either pulsed overnight with 10 l. or infected with recombinant vaccinia virus (multiplicity of infection=100) for 1 hour, then washed. In both cases they were labeled overnight with 0.3 mCi (11.1 MBq) and used as targets (5000/well) the following day in a 6-hr $^{51}$Cr release assay with unstimulated cryopreserved PBMC from the same donor as effectors. The percentage specific release was calculated as 100 × (experimental $^{51}$Cr release − spontaneous release) / (maximum release − spontaneous release).

Peptide synthesis

A series 15-residue peptides covering the fraction of RT sequence (HXB.2 subclone of HTLVIII/B) (32) that was expressed by the virus v-pol-27 were synthesized and purified as described previously (13,36). Their molar concentration was determined by HPLC or by spectrophotometry. A series of analogs of peptide HP 138 have been synthesized on an ABI automated synthesizer, cleaved by low HF procedure, desalted either by P4-biogel or by reverse-phase (C18 Sep-Pak, Waters) chromatography, and when necessary purified to a single HPLC peak (C18 column, Waters). Amino acid analysis (performed by O. Bates and coll., University of California, Irvine) confirmed the expected sequences.

Patient source and clinical evaluation

HIV+ patients were obtained from Wilford Hall United States Air Force Medical Center, Lackland Air Force Base, Tex. Individuals were diagnosed as being HIV infected if anti-HIV antibodies were demonstrated on two specimens tested by the HIV enzyme immunoassay (Abbott Laboratories, Irving, Tex.) and confirmed by Western blot analysis (Roche Biomedical Laboratories, Burlington, N.C.). Patients were classified according to the Walter Reed Staging System (37). Lymphocyte counts and T cell subsets were determined using laser-based flow cytometry (Coulter Epics Profile, Coulter Electronics, Inc., Hialeah, Fla.) and OKT4A (anti-CD4) and OKT8 (anti-CDS) monoclonal antibodies (Ortho-diagnostics Systems, Raritan, N.J.).

EXAMPLE 1

Generation of a murine CTL line (Pol a) specific for the N-terminal end of HIV-1 reverse transcriptase: The CTL line Pol a was derived from spleen cells of C3H/HeJ mice immunized with the recombinant vaccinia virus v-pol and restimulated in vitro with an $H-2^k$ fibroblast line (L-pol) transfected with the same HIV-1 pol gene insert. This CTL line (FIG. 1) lysed specifically L-pol as well as untransfected $H-2^k$ fibroblasts (L-cells) infected by v-pol, but not L-cells infected by the control vaccinia virus v-ctrl. Therefore, the HIV-1 pol gene fragment expressed at least one CTL epitope recognized on $H-2^k$ fibroblasts.

To localize the epitope(s), L cells were first infected with recombinant vaccinia viruses expressing truncated versions of the pol gene (FIG. 1) and these cells were used as targets in a cytotoxicity assay with the Pol a CTL line. The targets infected with viruses containing from 100% to as little as 27% of the N-terminal part of the original insert were all lysed to a comparable extent (FIG. 1). This experiment indicated that an immunodominant epitope was present in the portion of the protein encoded by the shortest pol insert (27% of the original insert, i.e. residues 168 to 316). This area corresponds to the N-terminal end of RT. Other epitopes may have been present in the remainder of the sequence, but this portion by itself was able to induce maximal lysis.

EXAMPLE 2

Identification of the immunodominant epitope recognized by the line Pol a: To identify the epitope(s) contained in this area, we used 21 overlapping 15-amino acid peptides designated HP134 to HP154 covering residues 168 to 316. L-cells were incubated overnight with $^{51}Cr$ together with peptides (20 μM, and tested for lysis by Pol a. To reduce the number of different targets to be tested, we analyzed mixtures of two peptides at a time, but avoided mixing overlapping peptides that might have a higher risk of inhibiting each other by sharing the same MHC binding site. Because preliminary experiments had suggested that peptide HP138 was responsible for targeting the cytotoxic activity, HP138 was tested individually and found to sensitize targets (FIG. 2). However, none of the other peptides was able to sensitize targets (FIG. 2), including HP137 and 139 [that overlap HP138 by 9 and 5 residues, respectively] even when tested individually (data not shown). HP138 (CTEMEKEGKISKIGP) corresponds to residues 205-219 of the HTLV/IIIB strain sequence (32). The peptide is not toxic by itself as determined by spontaneous lysis and cell recovery in the presence of peptide alone (data not shown). The line Pol a was Class I MHC-restricted because it killed HP 138-pulsed, Class II MHC molecule-negative $H-2^k$ L-cell fibroblasts, but not 3T3 fibroblasts ($H-2^d$) or EL4 thymoma cells ($H-2^b$). It was demonstrated to be CD4-CD8+ by treatment with anti-CD8 or anti-CD4 monoclonal antibodies and complement (data not shown).

DEFINITION OF OPTIMAL EPITOPES

Because HP138 sensitized targets best at high concentrations (20 μM) a series of peptide analogs were synthesized and purified in the area of HP138 to determine whether activity could be improved by extending or shortening the peptide by a few residues. The addition of two amino acids (FIG. 3) on the N-terminal side of the sequence (peptide 203-219) induced both a higher maximal specific release (more than 60% vs 40%) and a 30-fold lower concentration needed to obtain half-maximal activity (about 0.3 μM vs 10 μM). In contrast, removal of residues 205 and 206 at the N-terminus abrogated all activity (peptide 207-223 compare to 205-223). This result suggests that a critical determinant is at the N-terminus of HP 138. The addition of amino acids on the C-terminal end of 205-219 (peptide 205-223) also enhanced the activity (plateau at 60%, half-maximal lysis at about 1 μM) but was not able to restore the loss of activity when residues 205 and 206 were missing in peptide 207-223. Peptide 199-223 contained both the two residues 203 and 204 and the elongation on the C terminus that enhanced the activity in 205-223, but surprisingly its activity was not better than that of 205-223 (same maximal activity, half-maximal lysis at about 2 μM), as if the sequence 199-202 was partly inhibiting the recognition. Finally, the removal of the proline residue 219 did not modify the maximal activity of peptide 203-219 but increased slightly the concentration necessary for half-maximal lysis ( 1 μM, peptide 203-218) .

RECOGNITION OF THE EPITOPE BY HUMAN CYTOTOXIC CELLS

In order to determine whether the epitope for CD8+ class I MHC-restricted CTL identified in the mouse model would be recognized by cells from HIV-infected humans, PBMC from 2 HIV seropositive and 2 seronegative individuals were tested, without restimulation in vitro, for the lysis of autologous EBV-transformed cells incubated overnight with peptides 205-219 (FIG. 4, upper panel). The PBMC from both patients were able to kill specifically targets preincubated with the two peptides, but not targets preincubated with a control peptide or with medium only. Conversely, the PBMC from both seronegative donors failed to kill the targets incubated with either peptide, but did show some killing on autologous target cells infected with the control vaccinia virus (FIG. 4, lower panel). The latter cytolytic activity probably is a memory response resulting from a prior smallpox vaccination. Two patients, but not the healthy controls, also showed a high cytotoxic activity against the targets infected with the pol-recombinant vaccinia virus (FIG. 4, lower panel). For one of these two donors (patient 2) the phenotype of the effector cells was tested. The activity was blocked by anti-CD3 and anti-CD8, but not by anti-CD4 monoclonal antibodies and complement, and was genetically restricted (data not shown). Thus, these cells were conventional antigen specific MHC restricted CD8+ CTL. The cells from 12 HIV seropositive patients and 5 controls have been tested (FIG. 5). The level of killing after incubation of the target cells with HP138, peptide 203-219 or 205-219 was higher than 10% in 5 of the 12 patients, whereas it ranged from <0 to 3.2% in the seronegative donors.

The epitope 203-219 is in a region highly conserved in evolution among reverse transcriptase genes of other viruses. For this reason it is likely to be essential for RT activity and may, therefore, not tolerate substitutions required for escape from the immune system. When the residues 203-219 and 205-219 were compared, it was shown that the two residues (203 and 204) enhanced dramatically the activity of the original peptides, whereas the analog missing residues 205 and 206 had no activity at all. Thus, the sequence 203-206 seems essential for optimal activity of the peptide. It is also possible to enhance the activity by elongating the original peptide on the C-terminal side. Interestingly, a longer analog encompassing both the N- and C- terminal extensions did not reach the same level of activity as the optimal epitope 203-219. Additional residues contained on the N-terminal side may include a hindering structure similar to those found in Class-II restricted epitopes.

The peptides of the invention should preferably contain at least 15 amino acids, though it may contain as many as 40 amino acids. However, at least 12 amino acids should show homology to the most preferred 17 amino acid sequence. In any case, the Cys-Thr peptides should be conserved. The cysteine amide of the preferred peptide Glu-Ile-Cys-Thr-Glu-Met-Glu-Lys-Glu-Gly-Lys-Ile-Ser-Lys-Ile-Gly-Pro is particularly preferred.

The peptides of the invention may be given in the usual carriers containing adjuvants such as alum and Freund's adjuvant. A preferred composition would contain the peptides in an emmulsion, which would protect the peptide and which provide for slow release delivery.

The preparations of the invention can be given parenterally. Preferred means of administration are subcutaneous, intramuscular or intravenous routes. A preferred method of administrations is by intravenous route. Interleukin 2 or other response potentiators may be given simultaneously either as a component of the composition containing the peptide or as a seperate injection. Such potentiators include but are not limited to interleukin 4, muramyl-dipeptide, adjuvants such alum or Freund's adjuvant or mycobacterium or mycobacterial products such as BCG. The peptides given as immune therapy may be given intravenously initially with repeat injections at 1 to 3 day intervals thereafter until desired level of T cell activity is evidenced. The physician may then monitor killer T cell activity and repeat the protocol when a decrease in killer T cell activity is observed.

The peptides of the invention may or may not raise antibodies to the HIV virus. Since the killer T-cells affect the infectivity of the HIV virus present in any cell in the body, it may be possible to treat individuals that have been exposed to the HIV virus before sufficient exposure to viral protein to raise antibodies. Hence, the therapy may prevent such individuals from becoming sero-positive.

Since T-cell response is often raised before any antibodies are found in the blood in measurable amounts, the peptides of the invention can be used to test for latent infection by exposing the donor cells to the peptides and testing for T cell response. Hence, the peptides are useful as part of a diagnositic kit to screen seronegative blood donors or other individuals.

REFERENCES

1. Pasternack, M. S. (1988) *Adv. Intern. Med.* 33, 17-44.
2. Earl, P. L., Moss, B., Morrison, R. P., Wehrly, K., Nishio, J. & Chesebro, B. (1986) *Science* 234, 728.
3. Plata, F., Langlade-Demoyen, P., Abastado, J. P., Berbar, T. & Kourilsky, P. (1987) *Cell* 48, 231-240.
4. Walker, C. M., Moody, D. J., Stites, D. P. & Levy, J. A. (1986) *Science* 234, 1563-1566.
5. Tsubota, H., Lord, C. I., Watkins, D. I., Morimoto, C. & Letvin, N. L. (1989) *J. Exp. Med.* 169, 1421-1434.
6. Walker, B. D., Chakrabarti, S., Moss, B., Paradis, T. J., Flynn, T., Durno, A. G., Blumberg, R. S., Kaplan, J. C., Hirsch, M. S. & Schooley, R. T. (1987)*Nature* 328, 345-351.
7. Walker, B. D., Flexner, C., Paradis, T. J., Fuller, T. C., Hirsch, M. S., Schooley, R. T. & Moss, B. (1988) *Science* 240, 64-66.
8. Langlade-Demoyen, P., Michel, F., Hoffenbach, A., Vilmer, E., Dadaglio, G., Garicia-Pons, F., Mayaucd, C., Autran, B., Wain-Hobson, S. & Plata, F. (1988) *J. Immunol.* 141, 1949-1957.
9. Riviere, Y., Tanneau-Salvadori, F., Regnault, A., Lopez, O., Sansonetti, P., Guy, B., Kieny, M. P., Fournel, J. J. & Montagnier, L. (1989) *Journal of Virology* 63, 2270-2277.
10. Sethi, K. K., Näher, H. & Stroehmann, I. (1988) *Nature* 335, 178-181.
11. Shepp, D. H., Daguillard, F., Mann, D. & Quinnan, G. V. (1988) *AIDS* 2, 113-117.
12. Koup, R. A.. Sullivan, J. L., Levine, P. H., Brettler, D., Mahr, A., Mazzara, G., McKenzie, S. & Panicali, D. (1989) *Blood* 73, 1909-1914.
13. Takahashi, H., Cohen, J., Hosmalin, A., Cease, K. B., Houghten, R., Cornette, J., Delisi, C., Moss, B., Germain, R. N. & Berzofsky, J. A. (1988) *Proc. Natl. Acad. Sci. USA* 85, 3105-3109.
14. Rosenberg, Z. F. & Fauci, A. S. (1989) *Adv. Immunol.* 47, 377-431.
15. Takahashi, H., Houghton; R., Putney, S. D., Margulies, D. H., Moss, B., Germain, R. N. & Berzofsky, J. A. (1989) *J. Exp. Med.,* in press.
16. Takahashi, H., Merli, S., Pumey, S. D., Houghton, R., Moss, B., Germain, R. N. & Berzofsly,, J. A. (1989) *Science* 246, 118-121.
17. Robinson, W. E. Jr., Montefiori, D. C., Mitchell, W. M., Prince, A. M., Alter, H. J., Dreesman, G. R. & Eichberg, J. W. (1999) *Proc. Natl. Acad. Sci. U.S.A.* 86, 4710-4714.
18. Takeda, A., Tuazon, C. U. & Ennis, F. A. (1988) *Science* 242, 580-583.
19. Weinhold, K. J., Lyerly, H. K., Stanley, S. D., Austin, A. A., Matthews, T. J. & Bolognesi, D. P. (1989) *J. Immununol.* 142, 3091-3097.
20. Siliciano, R. F., Trebor, L., Knall, C., Karr, R. W., Berman, P., Gregory, T. & Reinherz, E. L. (1988) *Cell* 54, 561-575.
21. Mittler, R. S. & Hoffmann, M. K. (1989) *Science* 245, 1380-1382.
22. Golding, H., Shearer, G. M., Hillman, K., Lucas, p., Manischewitz, J., Zajac, R. A., Clerici, M., Gress, R. E., Boswell, N. R. & Golding, B. (1989) *J. Clin. Invest.* 83, 1430-1435.

23. Townsend, A.R.M., Rothbard, J., Gotch, F. M., Bahadur, G., Wraith, D. & McMichael, A. J. (1986) *Cell* 44, 959–968.
24. Yewdell, J. W., Bennink, J. R., Smith, G. L. & Moss, B. (1985) *Proc. Natl. Acad. Sci. U.S.A.* 82, 1785–1789.
25. Kees, U. & Krammer, P. H. (1984) *J. Exp. Med.* 159, 365–377.
26. Yewdell, J. W., Bennink, J. R., Mackett, M., Lefrancois, L., Lyles, D. S. & Moss, B. (1986) *J. Exp. Med.* 163, 1529–1538.
27. Bangham, C. R. M., Openshaw, P. J. M., Ball, L. A., King, A. M. Q., Wertz, G. W. & Askonas, B. A. (1986) *J. Immunol.* 137, 3973–3977.
28. Puddington, L., Bevan, M. J., Rose, J. K. & Lefrancois, L. (1986) *Journal of Virology* 60, 708–717.
29. Claverie, J. M.., Kourilsky, P., Langlade-Demoyen, P., Chalufour-Prochnicka, A., Dadaglio, G., Tekaia, F., Plata, F. & Bougueleret, L. (1988) *Eur. J. Immunol.* 18, 1547–1553.
30. Nixon, D. F., Townsend, A. R. M., Elvin, J. G., Rizza, C. R., Gallwey, J. & McMichael, A. J. (1988) *Nature* 336, 484–487.
31. Flexner, C., Broyles, S. S., Earl, P., Chakrabarti, S. & Moss, B. (1988) *virology* 166, 339–349.
32. Ratner, L., Haseltine, W., Patarca, R., Livak, K. J., Starcich, B., Josephs, S. F., Doran, E. R., Rafalski, J. A., Whitehorn, E. A., Baumeister, K., Ivanoff, L., Petteway, S. R., Jr., Pearson, M. L., Lautenberger, J. A., Papas, T. S., Ghrayeb, J., Chang, N. T., Gallo, R. C. & Wong-Staal, F. (1985) *Nature* 313, 277–277.
33. Walker, B. D., Flexner, C., Birch-Limberger, K., Fisher, L., Paradis, T. J., Aldovini, A., Young, R., Moss, B. & Schooley, R. T. (1989) *Proc. Natl. Acad. Sci. U.S. A.*, in press.
34. Chakrabarti, S., Robert-Guroff, M., Wong-Staal, F., Gallo, R. C. & Moss, B. (1986) *Nature* 320, 535–537.
35. Margulies, D. H., Evans, G. A., Ozato, K., Camerini-Otero, R. D., Tanaka, K., Appella, E. & Seidman, J. G. (1983) *J. Immunol.* 130, 463.
36. Houghten, R. A. (1985) *Proc. Natl. Acad. Sci. USA.* 82, 5131–5135.
37. Redfield, R. R., Wright, D. C. & Tramont, E. C. (1986) *New Engl. J. Med.* 314, 131–132.
38. Myers, G., Josephs, S. F., Berzofsky, J. A., Rabson, A. B., Smith, T. F. & Wong-Staal, F. (1989) *Human retroviruses and AIDS* 1989 (Los Alamos National Laboratory, New Mexico).
39. Kumar, S., Miller, L. H., Quakyi, I. A., Keister, D. B., Houghten, R. A., Maloy, W. L., Moss, B., Berzofsky, J. A. & Good, M. F. (1988) *Nature* 334, 258–260.
40. Brett, S. J., Cease, K. B. & Berzofsky, J. A. (1988) *J. Exp. Med.* 168, 357–373.
41. Bodmer, H. C., Gotch, F. M. & McMichael, A. J. (1989) *Nature* 337, 653–655.
42. Vacchio, M. S., Berzofsky, J. A., Krzych, U., Smith, J. A., Hodes, R. J. & Finnegan, A. (1989) *J. Immunol.* 143, 2814–2819.
43. Margalit, H., Spouge, J. L., Cornette, J. L., Cease, K., Delisi, C. & Berzofsky, J. A. (1987) *J. Immunol.* 138, 2213–2229.
44. Good, M. F., Maloy, W. L., Lunde, M. N., Margalit, H., Cornette, J. L., Smith, G. L., Moss, B., Miller, L. H. & Berzofsky, J. A. (1987) *Science* 235, 1059–1062.
45. Good, M. F., Pombo, D., Quakyi, I. A., Riley, E. M., Houghten, R. A., Menon, A., Alling, D. W., Berzofsky, J. A. & Miller, L. H. (1988) *Proc. Natl. Acad. Sci. USA* 85, 1199–1203.
46. Dontfraid, F., Cochran, M. A., Pombo, D., Knell, J. D., Quakyi, I., Kumar, S., Houghten, R. A., Berzofsky, J. A., Miller, L. H. & Good, M. F. (1988) *Mol. Biol. Med.* 5, 185–196.
47. Hale, P. M., Cease, K. B., Houghten, R. A., Ouyang, C., Putney, S., Javaherian, K., Margalit, H., Cornette, J. L., Spouge, J. L., Delisi, C. & Berzofsky, J. A. (1989) *Internal. Immunol.* 1, 409–415.
48. Berzofsky, J. L., Bensussan, A., Cease, K. B., Bourge, J. F., Cheynier, R., Lurhuma, Z., Salaüin, J.-J., Gallo, R. C., Shearer, G. M. & Zagury, D. (1988) *Nature* 334, 706–708.
49. Clerici, M., Stocks, N. I., Zajac, R. A., Boswell, R. N., Bernstein, D. C., Mann, D. L., Shearer, G. M. & Berzofsky, J. A. (1989) *Nature* 339, 383–385.
50. Lamb, J. R., Eckels, D. D., Lake, P., Woody, J. N. & Green, N. (1982) *Nature* 300, 66–69.
51. Hurwitz, J. L., Heber-Katz, E., Hackett, C. J. & Gerhard, W. J. (1984) *J. Immunol.* 133, 3371–3377. 1
52. Achour, A., Fossati, I., Margaritte, C., Berzofsky, J. A., Gallo, R. C. & Zagury, D. (1989) *Vth International Conference on AIDS, Montreal* 546.(Abstract)
53. Kronenberg, M., Siu, G., Hood, L. E. & Shastri, N. (1986) *Annu. Rev. Immunol.* 4, 529–591.
54. Klein, J. & Figueroa, F. (1986) CRC *Crit. Rev. Immunol.* 6, 295–386.
55. Clerici, M., Stocks, N. I., Zajac, R. A., Boswell, R. N., Lucey, D. R., Via, C. S. & Shearer, G. M. (1989) *J. Clin. Invest.*, in press.

We claim:

1. A peptide consisting essentially of the following amino acid sequence:
Cys-Thr-Glu-Met-Glu-Lys-Glu-Gly-Lys-Ile-Ser-Lys-Ile-Gly-Pro.

2. A peptide consisting essentially of the following amino acid sequence: Glu-Ile-Cys-Thr-Glu-Met-Glu-Lys-Glu-Gly-Lys-Ile-Ser-Lys-Ile-Gly-Pro.

3. A cysteine amide of the peptide of claim 2.

* * * * *